(12) United States Patent
Wei

(10) Patent No.: US 11,562,829 B2
(45) Date of Patent: Jan. 24, 2023

(54) TASK-ORIENTED DIALOGUE SYSTEM WITH HIERARCHICAL REINFORCEMENT LEARNING

(71) Applicant: Zhongyu Wei, Shanghai (CN)

(72) Inventor: Zhongyu Wei, Shanghai (CN)

( * ) Notice: Subject to any disclaimer, the term of this patent is extended or adjusted under 35 U.S.C. 154(b) by 0 days.

(21) Appl. No.: 17/508,675

(22) Filed: Oct. 22, 2021

(65) Prior Publication Data

US 2022/0130546 A1   Apr. 28, 2022

(51) Int. Cl.

| | | |
|---|---|---|
| *G16H 50/20* | (2018.01) | |
| *G06N 3/08* | (2006.01) | |
| *G06N 3/04* | (2006.01) | |
| *A61B 5/00* | (2006.01) | |
| *G16H 10/60* | (2018.01) | |

(Continued)

(52) U.S. Cl.
CPC ............ *G16H 50/20* (2018.01); *A61B 5/7264* (2013.01); *A61B 5/7275* (2013.01); *G06N 3/0454* (2013.01); *G06N 3/08* (2013.01); *G06N 20/00* (2019.01); *G16H 10/60* (2018.01); *G16H 40/20* (2018.01)

(58) Field of Classification Search
CPC ........ G16H 10/00–80/00; G06N 3/00–99/007; A61B 1/00–2576/026
See application file for complete search history.

(56) References Cited

U.S. PATENT DOCUMENTS

| | | | |
|---|---|---|---|
| 2018/0046773 A1* | 2/2018 | Tang | G06N 7/005 |
| 2018/0165603 A1* | 6/2018 | Van Seijen | G06N 3/0454 |

(Continued)

FOREIGN PATENT DOCUMENTS

WO   WO-2021179625 A1 *  9/2021   ........... G06N 3/0445

OTHER PUBLICATIONS

Xu et al., "End-to-End Knowledge-Routed Relational Dialogue System for Automatic Diagnosis," The Thirty-Third AAAI Conference on Artificial Intelligence (AAAI-19), pp. 7346-7353. (Year: 2019).*

(Continued)

*Primary Examiner* — Jonathon A. Szumny
(74) *Attorney, Agent, or Firm* — Brad Bertoglio; Intelink Law Group, P.C.

(57) ABSTRACT

A hierarchical reinforcement learning system for automatic disease prediction, and method thereof, including an agent simulator module for simulating the acts of doctors; a user simulator module for simulating the acts of patients; a disease classifier module, and an internal critic module, wherein the agent simulator module includes a master module which is in a high level, and a plurality of worker modules which are in a low level; the plurality of worker modules each acts as a doctor from a specific department, while the master module appoints the plurality of worker modules to interact with the user simulator module for collecting information; wherein the master module activates the disease classifier module to output a prediction result when information collected from the plurality of worker modules is sufficient; wherein the internal critic module is configured for generating intrinsic reward to the plurality of worker modules, judging the termination condition for the plurality of worker modules, and wherein the user simulator module is configured for returning extrinsic reward to the mater module.

20 Claims, 2 Drawing Sheets

(51) Int. Cl.
    *G16H 40/20*     (2018.01)
    *G06N 20/00*     (2019.01)

(56) References Cited

U.S. PATENT DOCUMENTS

| | | | |
|---|---|---|---|
| 2019/0297033 A1 | 9/2019 | Harma | |
| 2019/0355471 A1* | 11/2019 | Peng | G06N 3/006 |
| 2022/0107628 A1* | 4/2022 | Naderializadeh | G06N 20/00 |

OTHER PUBLICATIONS

Kao et al., "Context-Aware Symptom Checking for Disease Diagnosis Using Hierarchical Reinforcement Learning," The Thirty-Second AAAI Conference on Artificial Intelligence (AAAI-18), pp. 2305-2313. (Year: 2018).*
Liu et al., "Task-oriented Dialogue System for Automatic Diagnosis," Proceedings of the 56th Annual Meeting of the Association for Computational Linguistics (Short Papers), pp. 201-207 Melbourne, Australia, Jul. 15 -20, 2018. (Year: 2018).*
Tang et al., "Inquire and Diagnose: Neural Symptom Checking Ensemble using Deep Reinforcement Learning," 29th Conference on Neural Information Processing Systems (NIPS 2016), Barcelona, Spain, pp. 1-9. (Year: 2016).*
Dai et al., "A closed-loop healthcare processing approach based on deep reinforcement learning," Multimedia Tools and Applications, Published online Apr. 29, 2020. (Year: 2020).*
Edward Choi, Andy Schuetz, Walter F Stewart, and Jimeng Sun, "Using recurrent neural network models for early detection of heart failure onset," Journal of the American Medical Informatics Association, 24(2), 2017, 361-370 doi: 10.1093/jamia/ocw112, Advance Access Publication Date: Aug. 13, 2016.
Heriberto Cuay'Ahuitl, Simon Keizer, Oliver Lemon, Strategic Dialogue Management via Deep Reinforcement Learning, arXiv:1511.08099v1 [cs.AI] Nov. 25, 2015, Interaction Lab Department of Computer Science Heriot-Watt University Edinburgh.
Siddhartha R. Jonnalagadda , Abhishek K. Adupa, Ravi P. Garg, Jessica Corona-Cox & Sanjiv J. Shah, Text Mining of the Electronic Health Record: An Information Extraction Approach for Automated Identification and Subphenotyping of HFpEF Patients for Clinical Trials, Accepted: May 16, 2017 /Published online: Jun. 5, 2017, J. of Cardiovasc. Trans. Res. (2017) 10:313-321, Springer Science+Business Media New York.
Finale Doshi-Velez, PhD, Yaorong Ge, PhD and Isaac Kohane, Md, PhD, Comorbidity Clusters in Autism Spectrum Disorders: An Electronic Health Record Time-Series Analysis, Pediatrics vol. 133, No. 1, Jan. 2014.
Hao-Cheng Kao, Kai-Fu Tang, Edward Y. Chang, Context-Aware Symptom Checking for Disease Diagnosis Using Hierarchical Reinforcement Learning, HTC Research & Healthcare, The Thirty-Second AAAI Conference on Artificial Intelligence (AAAI-18), pp. 2305-2313.
Li Li, Wei-Yi Cheng, Benjamin S. Glicksberg, Omri Gottesman, Ronald Tamler, Rong Chen, Erwin P. Bottinger, Joel T. Dudley, Identification of type 2 diabetes subgroups through topological analysis of patient similarity, http://stm.sciencemag.org/, Oct. 28, 2015, vol. 7 Issue 311 311ra174, USA.
Xiujun Li, Yun-Nung Chen, Lihong Li, Jianfeng Gao, Asli Celikyilmaz, End-to-End Task-Completion Neural Dialogue Systems, Proceedings of the The 8th International Joint Conference on Natural Language Processing, pp. 733-743, Taipei, Taiwan, Nov. 27-Dec. 1, 2017, Microsoft Research, Redmond, WA, USA.
Bing Liu, Gokhan Tür, Dilek Hakkani-Tür, Pararth Shah, Larry Heck, End-to-End Optimization of Task-Oriented Dialogue Model with Deep Reinforcement Learning, Carnegie Mellon University, Pittsburgh, PA 15213, Google Research, Mountain View, CA 94043, arXiv:1711.10712v2 [cs.CL] Nov. 30, 2017.
Volodymyr Mnih, Koray Kavukcuoglu, David Silver, Andrei A. Rusu, Joel Veness, Marc G. Bellemare, Alex Graves, Martin Riedmiller, Andreas K. Fidjeland, Georg Ostrovski, Stig Petersen, Charles Beattie, Amir Sadik, Ioannis Antonoglou, Helen King, Dharshan Kumaran, Daan Wierstra, Shane Legg & Demis Hassabis, Human-level control through deep reinforcement learning, Feb. 26, 2015 | vol. 518| Nature | 529, Macmillan Publishers Limited, Letter, Google DeepMind, 5 New Street Square, London EC4A 3TW, UK.
Baolin Peng, Xiujun Li, Jianfeng Gao, Jingjing Liu, Yun-Nung Chenz, Kam-Fai Wong, Adversarial Advantage Actor-Critic Model for Task-Completion Dialogue Policy Learning, Microsoft Research, Redmond, WA, USA, The Chinese University of Hong Kong, Hong Kong, National Taiwan University, Taipei, Taiwan, arXiv:1710.11277v2 [cs.CL] Feb. 8, 2018.
Baolin Peng, Xiujun Li, Lihong Li, Jianfeng Gao, Asli Celikyilmaz, Sungjin Lee, Kam-Fai Wong, Composite Task-Completion Dialogue Policy Learning via Hierarchical Deep Reinforcement Learning, Microsoft Research, Redmond, WA, USA, The Chinese University of Hong Kong, Hong Kong, Proceedings of the 2017 Conference on Empirical Methods in Natural Language Processing, pp. 2231-2240, Copenhagen, Denmark, Sep. 7-11, 2017.
Jost Schatzmann, Blaise Thomson, Kari Weilhammer, Hui Ye and Steve Young, Agenda-Based User Simulation for Bootstrapping a POMDP Dialogue System, Cambridge University Engineering Department Trumpington Street, Cambridge, CB21PZ, United Kingdom, Proceedings of NAACL HLT 2007, Companion Volume, pp. 149-152, Rochester, NY, Apr. 2007.
Jost Schatzmann, Karl Weilhammer, Matt Stuttle, Steve Young, A Survey of Statistical User Simulation Techniques for Reinforcement-Learning of Dialogue Management Strategies, The Knowledge Engineering Review, 2006, vol. 00:0, 1-24, Cambridge University Press.
Chaitanya Shivade, Preethi Raghavan, Eric Fosler-Lussier, Peter J Embi, Noemie Elhadad, Stephen B. Johnson, Albert M Lai, A review of approaches to identifying patient phenotype cohorts using electronic health records, Shivade C, et al. J Am Med Inform Assoc 2014;21:221-230. doi:10.1136/amiajnl-2013-001935.
Pei-Hao Su, Milica Gašić, Nikola Mrkšić, Lina Rojas-Barahona, Stefan Ultes, David Vandyke, Tsung-Hsien Wen and Steve Young, Continuously Learning Neural Dialogue Management, Department of Engineering, University of Cambridge, Cambridge, UK, arXiv:1606.02689v1 [cs.CL] Jun. 8, 2016.
Kai-Fu Tang, Hao-Cheng Kao, Chun-Nan Chou, Edward Y. Chang, HTC Research, Taipei, Inquire and Diagnose: Neural Symptom Checking Ensemble using Deep Reinforcement Learning, 29th Conference on Neural Information Processing Systems (NIPS 2016), Barcelona, Spain.
Huaixiao Tou, Lu Yao, Zhongyu Wei, Xiahai Zhuang and Bo Zhang, Automatic infection detection based on electronic medical records, From Biological Ontologies and Knowledge bases workshop at IEEE BIBM 2017 Kansas City, MO, USA. Nov. 14, 2017, Creative Commons Attribution 4.0.
Tsung-Hsien Wen, David Vandyke, Nikola Mrksic, Milica Gasic, Lina M. Rojas-Barahona, Pei-Hao Su, Stefan Ultes, and Steve Young, A Network-based End-to-End Trainable Task-oriented Dialogue System, Cambridge University Engineering Dept., Trumpington Street, Cambridge, CB2 1PZ, UK, Proceedings of the 15th Conference of the European Chapter of the Association for Computational Linguistics: vol. 1, Long Papers, pp. 438-449, Valencia, Spain, Apr. 3-7, 2017.
Zhao Yan, Nan Duan, Peng Chen, Ming Zhou, Jianshe Zhou and Zhoujun Li, Building Task-Oriented Dialogue Systems for Online Shopping, 2017, State Key Lab of Software Development Environment, Beihang University, Beijing, China, Microsoft Research, Beijing, China, Microsoft Xiaoice Team, Beijing, China, BAICIT, Capital Normal University, Beijing, China, Association for the Advancement of Artificial Intelligence (www.aaai.org).
Steve Yooung, Fellow IEEE, Milica GaŠić, Member IEEE, Blaise Thomson, Member IEEE, and Jason D. Williams, Member IEEE, POMDP-Based Statistical Spoken Dialog Systems: A Review, Proceedings of the IEEE | vol. 101, No. 5, May 2013, Fudan University.
Tao Zhenga, Wei Xiec, Liling Xub, Xiaoying Hed, Ya Zhanga, Mingrong Youe, Gong Yange,You Chen (Ph.D), A machine learning-based framework to identify type 2 diabetes through electronic health records, International Journal of Medical Informatics 97 (2017) 120-127, Elsevier Ireland Ltd.

(56) References Cited

OTHER PUBLICATIONS

Chaitanya Shivade, Preethi Raghavan, Eric Fosler-Lussier, Peter J Embi, Noemie Elhadad, Stephen B Johnson, Albert M Lai; A review of approaches to identifying patient phenotype cohorts using electronic health records; Shivade C, et al. J Am Med Inform Assoc 2014;21:221-230. doi:10.1136/amiajnl-2013-001935; Downloaded from https://academic.oup.eom/jamia/article/21/2/221/2909214 by guest on Apr. 15, 2022.
Siddhartha R. Jonnalagadda, Abhishek K. Adupa, Ravi P. Ggarg, Jessica Corona-Cox & Sanjiv J. Shah; Text Mining of the Electronic Health Record: An Information Extraction Approach for Automated Identification and Subphenotyping of HFpEF Patients for Clinical Trials; J. of Cardiovasc. Trans. Res. (2017) 10:313-321; Springer Science+Business Media New York 2017.
Finale Doshi-Velez, PhD, Yaorong Ge, PhD and Isaac Kohane, MD, PhD; Comorbidity Clusters in Autism Spectrum Disorders: An Electronic Health Record Time-Series Analysis; American Academy of Pediatrics; www.pediatrics.org/cgi/doi/10.1542/peds.2013-0819 doi:10.1542/peds.2013-0819 Accepted for publication Oct. 22, 2013.
Qianlong Liu, Zhongyu Wei, Baolin Peng, Xiangying Dai, Huaixiao Tou, Ting Chen, Xuanjing Huang, Kam-fai Wong; Task-oriented Dialogue System for Automatic Diagnosis; Proceedings of the 56th Annual Meeting of the Association for Computational Linguistics (Short Papers), pp. 201-207 Melbourne, Australia, Jul. 15-20, 2018.
Lin Xu, Qixian Zhou, Ke Gong, Xiaodan Liang, Jianheng Tang, Liang Lin; End-to-End Knowledge-Routed Relational Dialogue System for Automatic Diagnosis; The Thirty-Third AAAI Conference on Artificial Intelligence (AAAI-19); pp. 7346-7353.
Ronald Parr and Stuart Russell; Reinforcement Learning with Hierarchies of Machines; This research was supported in part by ARO under the MURI program "Integrated Approach to Intelligent Systems," grant No. DAAH04-96-1-0341; pp. 1043-1049.
Richard S. Sutton, Doina Precup, Satinder SINGH; Between MDPs and semi-MDPs: A framework for temporal abstraction in reinforcement learning; Artificial Intelligence 112 (1999) 181-211; Published by Elsevier Science B.V.
Jing Zhang, Bowen Hao, Bo Chen, Cuiping Li, Hong Chen, Jimeng Sun; Hierarchical Reinforcement Learning for Course Recommendation in MOOCs; The Thirty-Third AAAI Conference on Artificial Intelligence (AAAI-19); pp. 435-442; Association for the Advancement of Artificial Intelligence (www.aaai.org).
Jiaping Zhange, Tiancheng Zhao, Zhou Yu; Multimodal Hierarchical Reinforcement Learning Policy for Task-Oriented Visual Dialog; Proceedings of the SIGDIAL 2018 Conference, pp. 140-150, Melbourne, Australia, Jul. 12-14, 2018; 2018 Association for Computational Linguistics.
Jun Fengz, Minlie Huangz, Yijie Zhangx, Yang Yangy, and Xiaoyan Zhu; Relation Mention Extraction from Noisy Data with Hierarchical Reinforcement Learning; arXiv:1811 01237v1 [cs.CL] Nov. 3, 2018; Association for the Advancement of Artificial Intelligence (www.aaai.org).
Mohammad Ghavamzadeh; Hierarchical Reinforcement Learning in Continuous State and Multi-Agent Environments; pp. I-155; Submitted to the Graduate School of the University of Massachusetts Amherst in partial fulfillment of the requirements for the degree of Doctor of Philosophy; Sep. 2005.
Yu-Shao Peng, Kai-Fu Tang, Hsuan-Tien Lin, Edward Y. Chang; Refuel: Exploring Sparse Features in Deep Reinforcement Learning for Fast Disease Diagnosis; pp. 1-10; 32nd Conference on Neural Information Processing Systems (NeurIPS 2018), Montréal, Canada.
Tejas D. Kulkarni, Karthik R. Narasimhan, Ardavan Saeedi, Joshua B. Tenenbaum; Hierarchical Deep Reinforcement Learning: Integrating Temporal Abstraction and Intrinsic Motivation; pp. 1-9; 29th Conference on Neural Information Processing Systems (NIPS 2016), Barcelona, Spain.
Volodymyr Mnih, Koray Kavukcuoglu, David Silver, Andrei A. Rusu, Joel Veness, Marc G. Bellemare, Alex Graves, Martin Riedmiller, Andreas K. Fidjeland, Georg Ostrovski, Stig Petersen, Charles Beattie, Amir Sadik, Ioannis Antonoglou, Helen King, Dharshan Kumaran, Daan Wierstra, Shane Legg & Demis Hassabis; Human-level control through deep reinforcement learning; Letter; doi:10.1038/nature14236; Feb. 26, 2015, vol. 518, Nature, 529.
Hao-Cheng Kao, Kai-Fu Tang, Edward Y. Chang, Context-Aware Symptom Checking for Disease Diagnosis Using Hierarchical Reinforcement Learning; pp. 2305-2313; The Thirty-Second AAAI Conference on Artificial Intelligence (AAAI-18).
Xin Wang, Wenhu Chen, Jiawei Wu, Yuan-Fang Wang, William Yang Wang; Video Captioning via Hierarchical Reinforcement Learning; pp. 4213-4222; Open Access by Computer Vision Foundation.
Ryuichi Takanobu, Tianyang Zhang, Jiexi Liu, Minlie Huang, A Hierarchical Framework for Relation Extraction with Reinforcement Learning; The Thirty-Third AAAI Conference on Artificial Intelligence (AAAI-19); pp. 7072-7079; Association for the Advancement of Artificial Intelligence (www.aaai.org).
Jiaxian Guo, Sidi Lu, Han Cai, Weinan Zhang, Yong Yu, Jun Wang; Long Text Generation via Adversarial Training with Leaked Information; pp. 5141-5148; The Thirty-Second AAAI Conference on Artificial Intelligence (AAAI-18); Association for the Advancement of Artificial Intelligence (www.aaai.org).
Carlos Florensay, Yan Duanyz, Pieter Abbeel; Stochastic Neural Networks for Hierarchical Reinforcement Learning; pp. 1-17; arXiv:1704.03012v1 [cs.AI] Apr. 10, 2017; Published as a conference paper at ICLR 2017.
Ofir Nachum, Shixiang Gu, Honglak Lee, Sergey Levine; Data-Efficient Hierarchical Reinforcement Learning; pp. 1-11; 32nd Conference on Neural Information Processing Systems (NeurIPS 2018), Montréal, Canada.
Carlos Florensa, David Held, Xinyang Geng, Pieter Abbeel; Automatic Goal Generation for Reinforcement Learning Agents; Proceedings of the 35 th International Conference on Machine Learning, Stockholm, Sweden, PMLR 80, 2018.
Da Tang, Xiujun Li, Jianfeng Gao, Chong Wang, Lihong Li, Tony Jebara, Subgoal Discovery for Hierarchical Dialogue Policy Learning; arXiv:1804.07855v3 [cs.CL] Sep. 22, 2018.
Kai-Fu Tang, Hao-Cheng Kao, Chun-Nan Chou, Edward Y. Chang; Inquire and Diagnose: Neural Symptom Checking Ensemble using Deep Reinforcement Learning; pp. 1-9; 29th Conference on Neural Information Processing Systems (NIPS 2016), Barcelona, Spain.
Jost Schatzmann, Blaise Thomson, Karl Weilhammer, Hui Ye and Steve Young; Agenda-Based User Simulation for Bootstrapping a POMDP Dialogue System; Proceedings of IIIAACL HLT 2007, Con:PCfnion Volume, pp. 149-152, Rochester, NY, Apnl 2007. © 2007 Association for Computational Linguistics.
Zhongyu Wei; Task-oriented Dialogue System for Automatic Disease Diagnosis; Oct. 22, 2021; 17508655.
Volodymyr Mnih et al.; Human-level control through deep reinforcement learning; Feb. 26, 2015, vol. 518, Nature 529; Macmillan Publishers Limited.

\* cited by examiner

TASK-ORIENTED DIALOGUE SYSTEM WITH HIERARCHICAL REINFORCEMENT LEARNING

The present patent application claims a priority to China application No. 202011135075.2, filed on Oct. 22, 2020, and a priority to China application No. 202011136008.2, filed on Oct. 22, 2020. The entire content of each applications is incorporated herein by reference.

TECHNICAL FIELD

This invention is related to a system for automatic disease diagnosis, and more particularly, to a task-oriented dialogue system for automatic disease diagnosis with hierarchical reinforcement learning. This invention is also related to a method thereof.

BACKGROUND

With the development of electronic health records (EHRs) systems, researchers explore different machine learning approaches for automatic diagnosis ("A review of approaches to identifying patient phenotype cohorts using electronic health records", Shivade et al., 2013, Journal of the American Medical Informatics Association). Although impressive results have been reported for the identification of various disease, they rely on well established EHRs which are labor-intensive to build. Moreover, supervised model trained for one disease is difficult to be transferred to another, therefore, EHRs are needed for every single disease.

In order to relieve the pressure for constructing EHRs, researchers introduce task-oriented dialogue system to request symptoms automatically from patients for disease diagnosis. They formulate the task as Markov Decision Processes (MDPs) and employ reinforcement learning (RL) based methods for the policy learning of the system. Existing framework utlizes a setting of flat policy that treats diseases and all related symptoms equally. Although RL-based approaches have shown positive results for symptom acquisition, when it comes to hundreds of diseases in real environment, the setting of flat policy is quite impractical.

In general, a particular disease is related to a certain group of symptoms. That's to say, a person who suffers a disease will often carries some corresponding symptoms at the same time. As shown in FIG. 1, the correlation between diseases and symptoms is presented. X-axis represents symptoms and y-axis is the proportion of diseases related. Some patterns can be easily identified. In other word, each disease has a group of corresponding symptoms and the overlap among different groups of symptoms are limited. This motivates us to classify diseases into different groups following the setting of departments in the hospital and design a hierarchical structure for symptom acquisition and disease diagnosis.

Recently, Hierarchical Reinforcement Learning (HRL), in which multiple layers of policies are trained to perform decision making, has been successfully applied to different scenarios, including course recommendation, visual dialogue, relation extraction, etc. The natural hierarchy of target tasks are modeled either manually or automatically. Inspired by these research, it is explored to utilize the clustering information of diseases via HRL to deal with the issue of large action space.

HRL has a hierarchical policy and has been proposed to solve the problems with large action space. One classic framework of HRL is options framework ("Between mdps and semi-mdps: A framework for temporal abstraction in reinforcement learning", Sutton et al., Artificial Intelligence, 1999), which involves abstractions over action space. At each step, the agent chooses either a one-step "primitive" action or a "multi-step" action (option). Kulkarni, et al. proposed a hierarchical-DQN ("Hierarchical deep reinforcement learning: Integrating temporal abstraction and intrinsic motivation", arXiv preprint: arXiv:1604.06057, 2018), which integrates deep Q-learning into HRL, to learn policies for different levels simultaneously. HRL has been successfully applied to different tasks and reached promising results. Most existing works decompose the corresponding task into two steps manually, where the first step is finished by high level policy while the second step is finished by the low level policy. The task-specific design limits the generalization of HRL to complex tasks. Carlos et al. proposed a general framework ("Stochastic neural networks for hierarchical reinforcement learning", arXiv preprint: arXiv:1704.03012, 2017) that first learns useful skills (high level policies) in an environment and then leverages the acquired skills for learning faster in downstream tasks. Moreover, some methods that generate or discover goals automatically when training the policies of two levels have also been proposed.

There are some previous works that applies the flat RL-based method in the medical dialogue system and generates positive results. In the work of Wei et al. and Xu, et al., both symptoms and diseases are treated as actions and a flat policy is used for choosing actions ("Task-oriented dialogue system for automatic diagnosis", in Proceedings of the 56th Annual Meeting of the Association for Computational Linguistics, 2018; and "End-to-end knowledge-routed relational dialogue system for automatic diagnosis", arXiv preprint: arXiv:1901.10623, 2019). Considering the grouping between different diseases, Tang et al. divide diseases into different groups based on anatomy and trained a policy for each group of diseases ("Inquire and diagnose: Neural symptom checking ensemble using deep reinforcement learning", in Proceedings of NIPS Workshop on Deep Reinforcement Learning, 2016). Moreover, a rule-based method is used to choose a policy when interacting with patients. Based on the work of Tang et al., Kao et al. train a policy while fixing the policies of different groups to replace the rule-based method ("Context-aware symptom checking for disease diagnosis using hierarchical reinforcement learning", 2018). Due to the separate training of high level and low level policy, the whole system may reach a sub-optimal solution. In addition, the action of informing disease to the user is taken by the low level policy rather than the high level policy, which can only have the diagnosis based on some limited information.

However, there is always a need to provide an improved system with hierarchy framework having outperforming performance.

SUMMARY

In this invention, we classify diseases into several groups and build a dialogue system with a hierarchy of two levels for automatic disease diagnosis using HRL methods. The high level policy consists of a model named master and the low level policy consists of several workers and a disease classifier. The master is responsible for triggering a model in the low level. Each worker is responsible for inquiring symptoms related to a certain group of disease while disease classifier is responsible for making the final diagnosis based on information collected by workers. The proposed framework imitates a group of doctors from different departments to diagnose a patient together. Among them, each worker acts like a doctor from a specific department, while the master acts like a committee that appoints doctors to interact with this patient. When information collected from workers are sufficient, the master would activate a separate disease classifier to make the diagnosis. Models in the two levels are trained jointly for better disease diagnosis. We build a large real-world dataset and a synthetic dataset for the evaluation of our model. Experimental results demonstrate that the performance of our hierarchical framework outperforms other state-of-the-art approaches on both datasets.

In one aspect of this invention, it is provided a hierarchical reinforcement learning system for automatic disease prediction, including an agent simulator module for simulating the acts of doctors;

a user simulator module for simulating the acts of patients;

a disease classifier module, and an internal critic module, wherein the agent simulator module includes a master module which is in a high level, and a plurality of worker modules which are in a low level; the plurality of worker modules each acts as a doctor from a specific department, while the master module appoints the plurality of worker modules to interact with the user simulator module for collecting information;

wherein the master module activates the disease classifier module to output a prediction result when information collected from the plurality of worker modules is sufficient; and wherein the internal critic module is configured for generating intrinsic reward to the plurality of worker modules, judging the termination condition for the plurality of worker modules, and wherein the user simulator module is configured for returning extrinsic reward to the mater module.

Preferably, the diseases are divided into a plurality of disease subsets, with each disease subset being associated with a plurality of symptoms subsets, the symptoms of each plurality of symptoms subsets are related to diseases, and the plurality of worker modules collect information from the user simulator module about symptoms of the symptoms subsets.

Preferably, the plurality of worker modules iteratively collect information from the user simulator module for a plurality of turns.

Preferably, at each turn of the plurality of turns, the master module decides whether to collect symptom information from the user simulator module or inform the user simulator module with prediction result.

Preferably, when the master module decides to collect symptom information from the user simulator module, it picks one worker module of the plurality of worker modules to interact with the user simulator module.

Preferably, when the master module decides to inform the user simulator module with prediction result, it activates the disease classifier module to output the predicted disease.

Preferably, the picked worker module interacts with the user simulator module until a subtask of the picked worker module is terminated.

Preferably, the picked worker module takes an inquiry action and then receives an intrinsic reward from the internal critic module.

Preferably, the disease classifier module is activated by the master module, it takes the state of the master module as input and outputs a vector which represents the probability distribution over all diseases.

Preferably, the disease with highest probability is returned to the user simulator module as the prediction result.

Preferably, the intrinsic reward equals +1, if the picked worker module requests a symptom that the simulated user suffers; the intrinsic reward equals −1, if there are repeated actions generated by the picked worker module, or the number of the subtask turns reaches a threshold; and otherwise the intrinsic reward equals 0.

Preferably, the subtask of the picked worker module is terminated as successful when the user simulator module responds "true" to the symptom requested by the picked worker, which means the current worker finishes the subtask by collecting enough symptom information.

Preferably, the subtask of the picked worker module is terminated as failed when there are repeated actions generated by the picked worker module, or the number of the subtask turns reaches a threshold.

Preferably, at the beginning of each dialogue session, the user simulator module samples a user goal from the training set randomly, and all the explicit symptoms of the sampled user goal are used for initializing the dialogue session.

Preferably, during the course of dialogue, the user simulator module interacts with the agent simulator module based on the user goal.

Preferably, the dialogue session will be terminated as successful if the agent simulator module make the correct diagnosis.

Preferably, the dialogue session will be terminated as failed if the informed disease is incorrect or the dialogue turn reaches a maximal turn, or if there are repeated actions taken by the system.

Preferably, a reward shaping is used to add auxiliary reward to the extrinsic reward.

In another aspect of this invention, it is provided a hierarchical reinforcement learning method for automatic disease prediction, including providing an agent simulator module for simulating the acts of doctors;

providing a user simulator module for simulating the acts of patients;

providing a disease classifier module, and providing an internal critic module, wherein the agent simulator module includes a master module which is in a high level, and a plurality of worker modules which are in a low level; the plurality of worker modules each acts as a doctor from a specific department, while the master module appoints the plurality of worker modules to interact with the user simulator module for collecting information;

wherein the master module activates the disease classifier module to output a prediction result when information collected from the plurality of worker modules is sufficient; and wherein the internal critic module is configured for generating intrinsic reward to the plurality of worker modules, judging the termination condition for the plurality of worker modules, and wherein the user simulator module is configured for returning extrinsic reward to the mater module.

BRIEF DESCRIPTION OF DRAWINGS

The foregoing summary, as well as the following detailed description, will be better understood when read in conjunction with the appended drawings. For the purpose of illustration, there is shown in the drawings certain embodiments of the present disclosure. It should be understood, however, that the invention is not limited to the precise arrangements and instrumentalities shown. The accompanying drawings, which are incorporated in and constitute a part of this specification, illustrate an implementation of systems and apparatuses consistent with the present invention and, together with the description, serve to explain advantages and principles consistent with the invention.

Wherein.

DETAILED DESCRIPTION OF THE EMBODIMENTS

Figure 1:
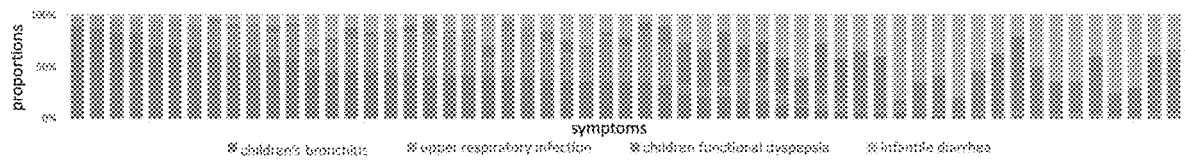
FIG. 1 illustratively shows the disease distribution over symptoms in the real world.

Before explaining at least one embodiment of the invention in detail, it is to be understood that the invention is not limited in its application to the details of construction and to the arrangements of the components set forth in the following description or illustrated in the drawings. The Figures and written description are provided to teach any person skilled in the art to make and use the inventions for which patent protection is sought. The invention is capable of other embodiments and of being practiced and carried out in various ways. Those skilled in the art will appreciate that not all features of a commercial embodiment are shown for the sake of clarity and understanding. Persons of skill in the art will also appreciate that the development of an actual commercial embodiment incorporating aspects of the present inventions will require numerous implementation—specific decisions to achieve the developer's ultimate goal for the commercial embodiment. While these efforts may be complex and time-consuming, these efforts nevertheless would be a routine undertaking for those of skill in the art having the benefit of this disclosure.

In addition, it is to be understood that the phraseology and terminology employed herein are for the purpose of description and should not be regarded as limiting. For example, the use of a singular term, such as, "a" is not intended as limiting of the number of items. Also the use of relational terms, such as but not limited to, "top," "bottom," "left," "right," "upper," "lower," "down," "up," "side," are used in the description for clarity in specific reference to the Figures and are not intended to limit the scope of the invention or the appended claims. Further, it should be understood that any one of the features of the invention may be used separately or in combination with other features. Other systems, methods, features, and advantages of the invention will be or become apparent to one with skill in the art upon examination of the Figures and the detailed description. It is intended that all such additional systems, methods, features, and advantages be included within this description, be within the scope of the present invention, and be protected by the accompanying claims.

Embodiments of the subject matter and the functional operations described in this specification optionally can be implemented in digital electronic circuitry, or in computer software, firmware, or hardware, including the structures disclosed in this specification and their structural equivalents, or in combinations of one or more of them. Embodiments of the subject matter described in this specification can, for example, be implemented as one or more computer program products, e.g., one or more modules of computer program instructions encoded on a computer readable medium for execution by, or to control the operation of, data processing apparatus.

The computer readable medium can be a machine readable tangible storage device, a machine readable tangible storage substrate, a tangible memory device, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A computer program (also known as a program, software, software application, script, or code), can be written in any form of programming language, including compiled or interpreted languages, and it can be deployed in any form, including as a stand alone program or as a module, component, subroutine, or other unit suitable for use in a computing environment. A computer program does not necessarily correspond to a file in a file system. A program can be stored in a portion of a file that holds other programs or data (e.g., on or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer readable media suitable for storing computer program instructions and data include all forms of nonvolatile memory, media, and memory devices, including by way of example semiconductor memory devices, e.g., EPROM, EEPROM, and flash memory devices; magnetic disks, e.g., internal hard disks or removable disks; magneto optical disks; and CD ROM and DVD ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) to LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any from, including acoustic, speech, or tactile input.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client server relationship to each other.

In this application, generally speaking, it is to provide a hierarchical reinforcement learning framework which could be used e.g. for disease prediction. It is to start with the flat policy setting and then introduce our hierarchical policy with two levels. Further it is to improve the performance of our model via reward shaping techniques.

As for RL-based models for automatic diagnosis, the action space of the agent (master-worker structure) $A=D \cup S$, where D is the set of all diseases and S is the set of all symptoms that associated with theses diseases. Given the state $s_t \in S$ at turn t, the agent takes an action according to it's policy $a_t \sim \pi(a|s_t)$ and receives an immediate reward $r_t = R(s_t, a_t)$ from the environment (patient/user). If $a_t \in S$, the agent chooses a symptom to inquire the patient/user. Then the user responds to the agent with {true/false/unknown} and the corresponding symptom will be represents via a 3-dim one-hot vector $b \in R^3$ accordingly. If $a_t \in D$, the agent informs the user with the corresponding disease as the diagnosis result and the dialogue session will be terminated as success/fail in terms of the correctness of diagnosis. The state $s_t = [b_1^T, b_2^T, \ldots, b_{|S|}^T]^T$, i.e., the concatenation of one-hot encoded statuses of each symptom, and not-requested symptoms until turn t are all encoded as b=[0,0,0].

The goal for the agent is to find an optimal policy so that it can maximizes the expected cumulative future discounted rewards $R_t = \Sigma_{t'=t}^T \gamma^{t'-t} r_{t'}$, where $\gamma \in [0,1]$ is the discounted factor and T is maximal turn of current dialogue session. The Q-value function $Q^\pi(s,a) = \mathbb{E}[R_t|s_t=s, a_t=a, \pi]$ is the expected return of taking action a in state s following a policy.

The optimal Q-value function is the maximum Q-value among all possible policies: $Q^*(s,a) = \max_\pi Q^\pi(s,a)$. It follows the Bellman equation:

$$Q^*(s, a) = \mathbb{E}_{s'}\left[r + \gamma \max_{a' \in \mathcal{A}} Q^*(s', a') \,\middle|\, s, a\right]$$

A policy $\pi$ is optimal if and only if for every state and action, $Q^\pi(s,a) = Q^*(s,a)$. Then the policy can be reduced deterministically by $\pi(a|s) = \text{argmax}_{a \in \mathcal{A}} Q^*(s,a)$.

In order to reduce the problem of large action space, in this application it is to extend the above RL formulation to a hierarchical structure with two-layer policies for automatic diagnosis. Following the options framework (see Sutton et al., "Between mdps and semi-mdps: A framework for temporal abstraction in reinforcement learning", Artificial Intelligence, 1999), our framework is designed as in FIG. 2.

Figure 2:
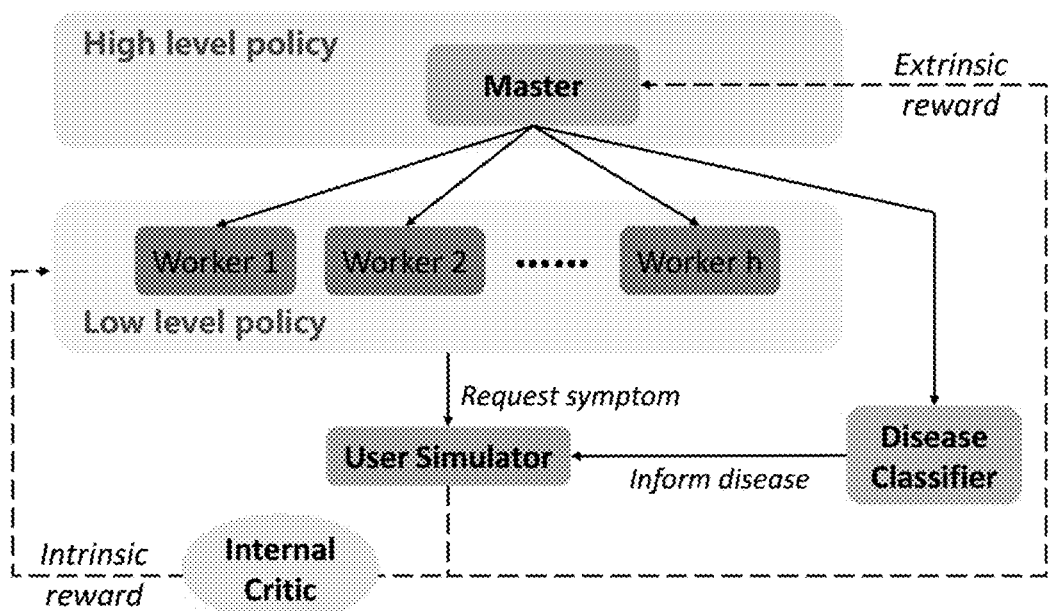
FIG. 2 illustratively shows the framework of the hierarchical reinforcement learning model with two-layer policies according to one embodiment of this application.

FIG. 2 illustratively shows the framework of the hierarchical reinforcement learning model with two-layer policies according to one embodiment of this application. There are four components in five framework: master, workers, disease classifier, internal critic and user simulator.

Specifically, we divide all the diseases in D into h subsets $D_1, D_2, \ldots, D_h$, where $D_1 \cup D_2 \cup \ldots \cup D_h = D$ and $D_i \cap D_j = \emptyset$ for any $i \neq j$ and i,j=1, 2, ... h. Each $D_i$ is associated with a set of symptoms $S_i \subseteq S$, whose symptoms are related to diseases in $D_i$. While worker $w^i$ is responsible for collecting information from user about symptoms of $S_i$.

At turn t, the master decides whether to collect symptom information from user (picking one worker to interact with user for several turns) or inform the user with diagnosis result (picking disease classifier to output the predicted disease). An illustration of the diagnosis process with interactions between models in two levels are presented in FIG. 3.

Figure 3:
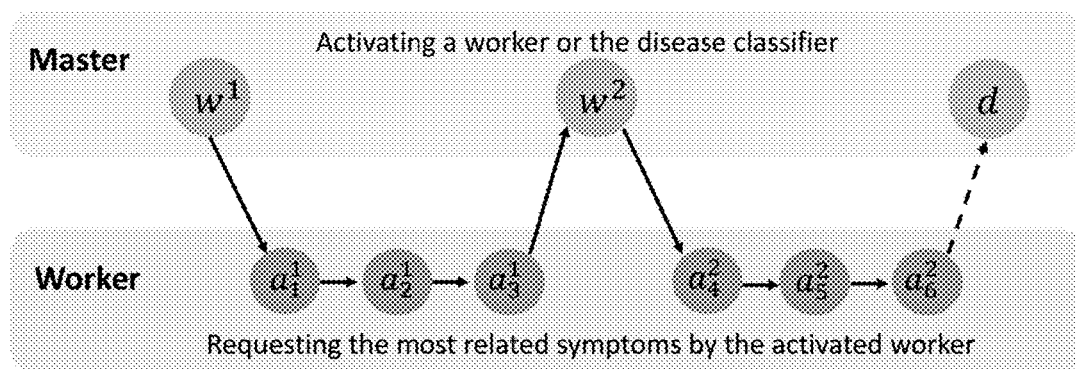
FIG. 3 illustratively shows the diagnosis process of the model according to one embodiment of this application.

FIG. 3 illustratively shows the diagnosis process of our model with interactions between models in two levels. $w^i$ is the action invoking worker, and d is the action invoking disease classifier. As for internal critic, it is responsible for both returning intrinsic reward to the worker and telling whether the subtask of the invoked worker is finished. In addition, the user simulator is applied to interact with the model in this application and return extrinsic reward.

The action space of master $A^m = \{w^i|i=1,2,\ldots,h\} \cup \{d\}$. The action indicates activating worker $w^i$, while d is a primitive action which means activating the disease classifier. At each turn t, the master takes the dialogue state $s_t \in S$ as input and takes an action $a_t^m \in A^m$ according to its policy $\pi^m(a_t^m|s_t)$. An extrinsic reward $r_t^e$ will be returned to master from the environment.

The decision process of master is not a standard MDP. Once the master activates a worker, this worker will interact with user for N turns until the subtask is terminated. Only after that master can take a new action and observe a new dialogue state.

As pointed out by Sutton et al., the learning problem of master can be formulated as a Semi-Markov Decision Process (SMDP), where the extrinsic rewards returned during the interaction between user and the chosen worker can be accumulated as the immediate rewards for the master (Ghavamzadeh, "Hierarchical reinforcement in continuous state and multi-agent environments", 2005). That is to say, after taking an action $a_t^m$, the reward $r_t^m$ for master can be defined as:

$$r_t^m = \begin{cases} \sum_{t'=1}^{N} \gamma^{t'} r_{t+t'}^e, & \text{if } a_t^m = w^i \\ r_t^e, & \text{if } a_t^m = d \end{cases}$$

where i=1, ..., h, $r_t^e$ is the extrinsic reward returned by the environment at turn t, γ is the discounted factor of the master and N is the number of primitive actions of worker. The Bellman equation for master can be written as follows:

$$Q_m(s, a^m) = r^m + \mathbb{E}_{(s',a^{m'})}[\gamma^N Q_m(s', a^{m'}) | s, a^m, \pi^m]$$

where s' is the observed dialogue state of master after it takes an action $a^m$, $a^{m'}$ is the next action when the state is s'.

The objective of master is to maximize the extrinsic reward through SMDP, thus the master's loss function can be written as follows:

$$\mathcal{L}(\theta_m) = \mathbb{E}_{s,a^m,r^m,s' \sim \mathcal{B}^m}[(y - Q_m(s, a^m; \theta_m))^2]$$

Where $y = r^m + \gamma^N \max_{a^{m'}} Q_m(s', a^{m'}; \theta_m^-)$, is the network parameter at current iteration, $\theta_m^-$ is the network parameter of previous iteration and $B^m$ is the fixed-length buffer of samples for master.

The worker $w^i$ corresponds to the set of diseases $D_i$ and the set of symptoms $S_i$. The action space of worker $w^i$ is: $A_i^w = \{\text{request}\}(\text{symptom})|\text{symptom} \in S_i\}$. At turn t, if worker $w^i$ is invoked, the current state of master $s_t$ will be passed to worker $w^i$, then worker $w^i$ will extract $S_t^i$ from $s_t$ and take $S_t^i$ as input and generate an action $a_t^i \in A_i^w$. The state extraction function is as follows:

$$s_t^i = \text{ExtractState}(s_t, w^i) = [b_{(1)}^{iT}, b_{(2)}^{iT}, \ldots, b_{(k_i)}^{iT}]^T$$

where $b_{(j)}^i$ is the representing vector of symptom $_{(j)} \in S_i$.

After taking action at $a_t^i \in A_i^w$, the dialogue is updated into $s_{t+1}$ and worker $w^i$ will receive an intrinsic reward $r_t^i$ from the module of internal critic. So the objective of worker is to maximize the expected cumulative discounted intrinsic rewards. The loss function of worker $w^i$ can be written as:

$$\mathcal{L}(\theta_w^i) = \mathbb{E}_{s^i,a^i,r^i,s^i \sim \mathcal{B}_i^w}[(y_i - Q_w^i(s^i, a^i, \theta_w^i))^2]$$

where $y_i = r^i + \gamma_w \max_{a^{i'}} Q_w^i(s^{i'}, a^{i'}; \theta_w^{i-})$, $\gamma_w$ is the discounted factor of all the workers, $\theta_w^i$ is the network parameter at current iteration, $\theta_w^{i-}$ is the network parameter of previous iteration and $B_i^w$ is the fixed-length buffer of samples for worker $w^i$.

Once the disease classifier is activated by master, it will take the master state $s_t$ as input and output a vector $p \in R^{|D|}$, which represents the probability distribution over all diseases. The disease with highest probability will be returned to the user as the diagnosis result. Two layers of Multi-Layered Perceptron (MLP) is utilized here for the disease diagnosis.

The internal critic is responsible for generating intrinsic reward $r_t^i$ to worker $w^i$ after an action $a_t^i$ is taken at turn t. $r_t^i$ equals +1, if the worker requests a symptom that the user suffers. If there are repeated actions generated by worker $w^i$ or the number of subtask turns reaches $T^{sub}$, $r_t^i$ would be -1. Otherwise, $r_t^i$ would be 0.

The internal critic is also responsible for judging the termination condition for the worker. In the task of this application, a worker is terminated as failed when there is repeated action generated or the number of subtask turns reaches $T^{sub}$. While a worker is terminated as successful when the user responds true to the symptom requested by the agent. Which means the current worker finishes the subtask by collecting enough symptom information.

Here it is to use a user simulator to interact with the agent. At the beginning of each dialogue session, the user simulator samples a user goal from the training set randomly. All the explicit symptoms of the sampled user goal are used for initializing a dialogue session. During the course of dialogue, the simulator interacts with the agent based on the user goal following some rules. One dialogue session will be terminated as successful if the agent make the correct diagnosis. It will be terminated as failed if the informed disease is incorrect or the dialogue turn reaches the maximal turn T. In order to improve the efficiency of the interaction, the dialogue would be terminated when repeated action is taken by the system.

In reality, the number of symptoms a patient suffers from is much less than the size of symptom set S and this results in a sparse feature space. In other words, it is hard for the agent to locate the symptoms that the user truly suffers from. In order to encourage master to choose a worker that can discover more positive symptoms, in this application it is to use the reward shaping method to add auxiliary reward to the original extrinsic reward while keeping the optimal reinforcement learning policy unchanged.

The auxiliary reward function from state $s_t$ to $s_{t+1}$ is defined as $f(s_t, s_{t+1}) = \gamma \phi(s_{t+1}) - \phi(s_t)$, $\phi(s)$, $\phi(s)$ is the potential function and can be defined as $$\phi(s) = \begin{cases} \lambda \times |\{j : b_j = [1, 0, 0]\}|, & \text{if } s \in S/S_\perp \\ 0, & \text{otherwise} \end{cases}$$

where $\phi(s)$ counts the number of true symptoms for a given state s, λ>0 is a hyper-parameter which controls the magnitude of reward shaping and $S_\perp$ is the terminal state set. Thus, the reward function for master will be changed into $$R_t^\phi = r_t + f(s_t, s_{t+1})$$

Both the master policy $\pi^m$ and each worker's policy $\pi_i^w$ are parameterized via Deep Q-Network (DQN, see Kulkarni et al., "Hierarchical deep reinforcement learning: Integrating temporal abstraction and intrinsic motivation", arXiv preprint:arXiv:1604.06057, 2018; and Mnih et al., "Human-level control through deep reinforcement learning", Nature, 2015). In DQN, the action is often selected following an ε-greedy policy. In our hierarchical framework, both the master and the workers behave following their own ε-greedy policy for training and greedy policy for testing.

During the training process, it is to store $(s_t, a_t^m, r_t^m, s_{t+N})$ in $B^m$ and $(s_t^i, a_t^w, r_t^i, s_{t+1}^i)$ in $B_i^w$.

At each training step, we perform experience replay to update the current networks for both master and workers in $B^m$ and $B_i^w$ respectively, while the target networks are fixed during experience replay. The target network will be updated (replaced by the current network) only when one experience replay is over. At each step, the current network will be evaluated on the training set, the experience buffer will be flushed only if the current network performs better than any previous versions in success rate. Therefore, the samples generated in the previous iterations will be removed from the experience buffer and it will speed up the training process. As for disease classifier, it will be updated with terminal states and corresponding disease labels after every 10 epochs' training of master.

Two datasets are constructed for the evaluation of the model of this invention. One is an extended version of an existing real-world dataset. Another is a synthetic dataset.

There is an existing dataset collected from real world for the evaluation of task-oriented DS for diagnosis (Weiet al., "Task-oriented dialogue system for automatic diagnosis", in Proceedings of the 56th Annual Meeting of the Association for Computational Linguistics, 2018). In this application we extend the original dataset following their labeling strategy. The newly constructed real-world dataset (RD) contains 1,490 user goals that belong to 4 diseases, namely, upper respiratory infection (URI), children functional dyspepsia (CFD), infantile diarrhea (ID) and children's bronchitis (CB). The raw data is collected from the pediatric department on a Chinese Online Healthcare Community (see http://muzhi.baidu.com).

Each user record consists of the self-report provided by the user and conversation text between the patient and a doctor. Experts with medical background identify symptom expressions and label them with three tags ("True", "False" or "UNK") to indicate whether the user suffers this symptom. After then, experts manually link each symptom expression to a concept on SNOMED CT (see https://www.snomed.org/snomed-ct). It is to note that, both self-reports and the conversations are labeled. Symptoms extracted from self-report are treated as explicit symptoms and the ones extracted from conversation are implicit symptoms. Statistics of RD dataset can be seen in Table 1.

TABLE 1

| disease | # of user goal | ave. # of ex. sym. | ave. # of im. sym. | # of sym. |
|---|---|---|---|---|
| ID | 450 | 2.22 | 4.68 | 83 |
| CFD | 350 | 1.73 | 5.05 | 81 |
| URI | 240 | 2.79 | 5.00 | 81 |
| CB | 450 | 3.01 | 5.35 | 84 |
| Total | 1490 | 2.44 | 3.68 | 90 |

Table 1 shows an overview of Real-world dataset (RD). # of user goal is the number of dialogue sessions of each disease; ave. # of ex. sym. And ave. # of im. sym. are the average number of explicit and implicit symptoms of user goals; # of sym. is the total number of symptoms that related to the disease.

In addition to the real-world dataset, in this application we build a synthetic dataset (SD). It is constructed based on symptom-disease database called SymCat (see www.symcat.com). There are 801 diseases in the database and we classify them into 21 departments (groups) according to International Classification of Diseases (ICD-10-CM) (see https://www.cdc.gov/nchs/icd/). We choose 9 representative departments from the database, each department contains top 10 diseases according to the occurrence rate in the Centers for Disease Control and Pre-vention (CDC) database.

In CDC database, each disease is linked with a set of symptoms, where each symptom has a probability indicating how likely the symptom is identified for the disease. Based on the probability distribution, we generate record one by one for each target disease. Given a disease and its related symptoms, the generation of a user goal follows two steps. First, for each related symptom, we sample the label for the symptom (true or false). Second, a symptom is chosen randomly from the set of all true symptoms to be the explicit one (same as symptoms extracted from self-report in RD) and rest of true symptoms are treated as implicit ones.

Table 2 shows an overview of the Synthetic Dataset (SD). Each user goal contains only 1 explicit symptom. The group id is correspond to the chapter in ICD-10-CM; # of diseases is the number of diseases included in this group.

TABLE 2

| disease tag: Cerebral edema | group id: 6 |
|---|---|
| explicit symptom | implicit symptom |
| headache: True | focal weakness: True |
| | diminished vision: True |
| | vomiting: True |
| | loss of sensation: True |

The description of SD dataset is shown in Table 3. The synthetic dataset we constructed contains 30,000 user goals, of which 80\% for training and 20\% for testing.

TABLE 3

| group id | # of user goal | # of diseases | ave. # of im. sym. | # of sym. |
|---|---|---|---|---|
| 1 | 3,371 | 10 | 3.23 | 65 |
| 4 | 3,348 | 10 | 1.71 | 89 |
| 5 | 3,355 | 10 | 2.67 | 68 |
| 6 | 3,380 | 10 | 2.83 | 58 |
| 7 | 3,286 | 10 | 2.78 | 46 |
| 12 | 3,303 | 10 | 2.04 | 51 |
| 13 | 3,249 | 10 | 2.48 | 62 |
| 14 | 3,274 | 10 | 1.58 | 69 |
| 19 | 3,389 | 10 | 2.91 | 73 |
| Total | 30,000 | 90 | 2.60 | 266 |

Experiments

The $\varepsilon$ for master and all the workers are all set to 0.1. For the master, the maximal dialogue turn T is set to 20, it will receive a extrinsic reward of +1 if the master inform the right disease. Otherwise, it will receive an extrinsic reward of −1 if the dialogue turn reaches the maximal turn or a wrong disease is informed. At non-terminal turns, the extrinsic reward is 0. Moreover, the sum of the extrinsic rewards (after reward shaping) over one subtask taken by a worker will be the reward for master. The maximal dialogue turn $T^{sub}$ is set to 5 for each worker.

For master and all the workers, the neural network of DQN is a three-layer network with two dropout layers and the size of hidden layer is 512, learning rate for the DQN network is set to 0.0005. All parameters are set empirically and settings for the two datasets are the same. In addition, all the workers are trained every 10 epochs seperately during the training process of master. For the disease classifier, the neural network is a two-layer network with a dropout layer and the size of hidden layer is 512, learning rate for the network is set to 0.0005. Moreover, it's trained every 10 epochs during the training process of master.

In the experiment the model of this invention is compared with some state-of-the-art reinforcement learning models for disease diagnosis.

Flat-DQN: This is the agent of Wei et al., (see "Task-oriented dialogue system for automatic diagnosis", in Proceedings of the 56th Annual Meeting of the Association for Computational Linguistics, 2018), which has one layer policy and an action space including both symptoms and diseases.

HRL-pretrained: This is a hierarchical model from Kao et al., (see "Context-aware symptom checking for disease diagnosis using hierarchical reinforcement learning", 2018). The setting is similar to ours, however, the low level policy is pre-trained first and then the high level policy is trained. Besides, there is no disease classifier for disease diagnosis specially and the diagnosis is made by workers.

It is to note that, for RL setting, the user goals are initialized with explicit symptoms, while implicit symptoms can only obtained via conversations.

In addition, we implement two models following supervised learning setting that treats the automatic diagnosis as a multi-class classification problem. Here is to report results of these two models for reference.

SVM-ex&im: This model takes symptoms representation (concatenation of $b_j$, where j=1,2, . . . , S) as input and predicts the target disease. Both explicit and implicit symptoms are used as input and SVM is used for classification. Because it obtains all implicit symptoms from the user, this model can be treated as the up-bound of RL-based models.

SVM-ex: This model takes only explicit symptoms as input and use SVM for classification. It can be treated as the baseline of RL-based models.

For both RD dataset and SD dataset, 80% of samples are used as training and 20% are used as testing. We use three metrics for the evaluation of the dialogue system following Wei et al. (see above) and Xu et al. ("End-to-end knowledge routed relational dialogue system for automatic diagnosis", arXiv preprint: arXiv:1901.10623, 2019), namely, success rate, average reward and the average number of turns per dialogue session. It is to note that the result of HRL-pretrained on RD dataset is missing because there is only one disease in each group and it is non-trivial to implement the multi-classification model for disease diagnosis.

Table 4 and Table 5 show the overall performance of different models on RD dataset and SD dataset respectively. We have following findings:

SVM-ex&im outperforms SVM-ex greatly on both two datasets, which indicates that implicit symptoms can improve the diagnosis accuracy significantly. Moreover, due to the lower overlap of symptoms between different diseases, the gap between SVM-ex&im and SVM-ex on SD dataset is much larger than the gap on RD dataset.

Due to the additional requested implicit symptoms, the Flat-DQN model, HRL-trained model and our HRL model reach a better diagnosis accuracy than SVM-ex on both datasets, which proves the efficiency by introducing reinforcement learning based models.

Compared to the baseline models, our HRL model takes more turns to have interactions with the user so that it can collect more information of their implicit symptoms. With more information about implicit symptoms, our HRL model significantly outperforms the other baselines in the diagnosis success rate.

Table 4 shows overall performance on RD dataset. The experiment is carried by 5 times and the final result is composed of the average and the standard error of 5 experiments.

TABLE 4

| Model | Success | Reward | Turn |
| --- | --- | --- | --- |
| SVM-ex | 0.663 ± .003 | \ | \ |
| Flat-DQN | 0.681 ± 0.018 | 0.509 ± 0.029 | 2.534 ± 0.171 |
| HRL-pretrained | \ | \ | \ |
| ours | 0.695 ± 0.018 | 0.521 ± 0.022 | 4.187 ± 0.187 |
| SVM-ex&im | 0.761 ± .006 | \ | \ |

Table 5 shows overall performance on SD dataset. The experiment is carried by 5 times and the final result is the average and the standard error of 5 experiments.

TABLE 5

| Model | Success | Reward | Turn |
| --- | --- | --- | --- |
| SVM-ex | 0.321 ± .008 | \ | \ |
| Flat-DQN | 0.343 ± 0.006 | 0.327 ± 0.003 | 2.455 ± 0.065 |
| HRL-pretrained | 0.452 ± 0.013 | 0.439 ± 0.023 | 6.838 ± 0.358 |
| ours | 0.504 ± 0.018 | 0.473 ± 0.056 | 12.959 ± 0.704 |
| SVM-ex&im | 0.732 ± .014 | \ | \ |

In order to evaluate the performance of different workers and disease classifier, we perform some additional experiments based on our HRL model.

Figure 4:
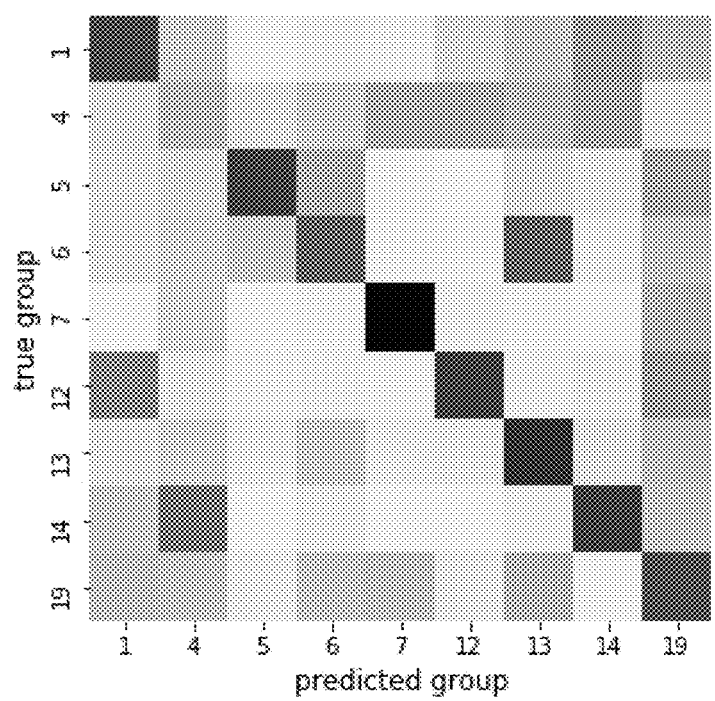
FIG. 4 illustratively shows the error analysis for the disease classifier in different groups on the HRL model according to one embodiment of this application.

In order to have deeper analysis of the user goals which have been informed the wrong disease by the agent, we collect all the wrong informed user goals and present the error matrix in FIG. 4.

FIG. 4 illustratively shows the error analysis for the disease classifier in different groups on our HRL model, the square with true group i and predicted group j means a disease in group i is misclassified into group j by the disease classifier, the darker the color, the higher the value.

It shows the disease prediction result for all the 9 groups. We can see the color of the diagonal square is darker than the others, which means most of wrong informed user goals are informed the disease in the same group. This is reasonable because diseases in the same groups usually share similar symptoms and are therefore more difficult to be distinguished.

Here we evaluate the performance of workers in terms of success rate, average intrinsic rewards and match rate. Match rate means the proportion of actions which have requested about the implicit symptoms that the user has.

Table 6 shows the performance of different workers in our HRL model. It can be seen there is positive correlation between the average intrinsic reward and the match rate, which means the more implicit symptoms a worker has requested from the user, the better of its performance.

TABLE 6

| group id | success rate | ave intrinsic reward | match rate | activation times |
| --- | --- | --- | --- | --- |
| 1 | 48.6% | 0.031 | 16.74% | 0.615 |
| 4 | 54.6% | −0.150 | 5.02% | 0.375 |
| 5 | 38.8% | −0.013 | 7.96% | 3.252 |
| 6 | 48.0% | −0.036 | 9.58% | 0.942 |
| 7 | 48.3% | 0.057 | 18.57% | 1.280 |

TABLE 6-continued

| group id | success rate | ave intrinsic reward | match rate | activation times |
|---|---|---|---|---|
| 12 | 43.0% | 0.021 | 11.26% | 0.666 |
| 13 | 52.4% | −0.138 | 7.18% | 0.823 |
| 14 | 72.2% | −0.111 | 3.77% | 0.614 |
| 19 | 47.4% | 0.031 | 22.72% | 1.124 |
| Average | 50.3% | −0.041 | 10.49% | 1.077 |

It will be appreciated by those skilled in the art that changes could be made to the embodiments described above without departing from the broad inventive concept thereof. It is understood, therefore, that the invention disclosed herein is not limited to the particular embodiments disclosed, but it is intended to cover modifications within the spirit and scope of the present invention as defined by the appended claims.

The invention claimed is:

1. A hierarchical reinforcement learning system for automatic disease prediction for a plurality of diseases, comprising:
one or more processors; and
a computer readable medium having encoded thereon computer-executable instructions to cause the one or more processors to:
model the acts of doctors with an agent simulator module, wherein the agent simulator module includes a master module which is in a high level, and a plurality of worker modules which are in a low level,
model the acts of patients with a user simulator module, wherein
the plurality of worker modules each acts as a doctor from a specific department, while the master module appoints the plurality of worker modules to interact with the user simulator module for collecting information, and
modeling the acts of doctors includes iteratively training each of the plurality of worker modules during a training process of the master module, wherein the iteratively training includes
storing, for each worker module, information collected by the worker module from interacting with the user simulator module in a respective experience buffer for the worker module,
performing experience replay to sample a subset of the collected information stored in the respective experience buffer for each worker module,
training a current neural network for each worker module based on its respective subset of the collected information,
updating a target neural network for each worker module based on the training, and
removing the subsets of collected information from the experience buffers after the updating;
produce a prediction result of the diseases of the plurality of diseases with a disease classifier module, wherein
the master module activates the disease classifier module to output the prediction result from the information collected from the plurality of worker modules, and
the prediction result is a probability distribution over all diseases of the plurality of diseases, and
produce an intrinsic reward with an internal critic module, wherein the internal critic module is configured to generate an intrinsic reward to the plurality of worker modules judging a termination condition for the plurality of worker modules, and
wherein the user simulator module is configured to return an extrinsic reward to the master module.

2. The hierarchical reinforcement learning system according to claim 1, wherein the diseases are divided into a plurality of disease subsets, with each disease subset being associated with a plurality of symptoms subsets, the symptoms of each plurality of symptoms subsets are related to diseases, and the plurality of worker modules collect information from the user simulator module about symptoms of the symptoms subsets.

3. The hierarchical reinforcement learning system according to claim 1, wherein the plurality of worker modules iteratively collect information from the user simulator module for a plurality of turns.

4. The hierarchical reinforcement learning system according to claim 3, wherein at each turn of the plurality of turns, the master module decides whether to collect symptom information from the user simulator module or inform the user simulator module with the prediction result.

5. The hierarchical reinforcement learning system according to claim 4, wherein when the master module decides to collect symptom information from the user simulator module, it picks one worker module of the plurality of worker modules to interact with the user simulator module.

6. The hierarchical reinforcement learning system according to claim 4, wherein when the master module decides to inform the user simulator module with prediction result, it activates the disease classifier module to output the predicted disease.

7. The hierarchical reinforcement learning system according to claim 5, wherein the picked worker module interacts with the user simulator module until a subtask of the picked worker module is terminated.

8. The hierarchical reinforcement learning system according to claim 7, wherein the subtask of the picked worker module is terminated as successful when the user simulator module responds "true" to the symptom requested by the picked worker, which means the current worker finishes the subtask by collecting enough symptom information.

9. The hierarchical reinforcement learning system according to claim 7, wherein the subtask of the picked worker module is terminated as failed when there are repeated actions generated by the picked worker module, or the number of the subtask turns reaches a threshold.

10. The hierarchical reinforcement learning system according to claim 5, wherein the picked worker module takes an inquiry action and then receives the intrinsic reward from the internal critic module.

11. The hierarchical reinforcement learning system according to claim 10, wherein the intrinsic reward equals +1, if the picked worker module requests a symptom that the simulated user suffers; the intrinsic reward equals −1, if there are repeated actions generated by the picked worker module, or the number of the subtask turns reaches a threshold; and otherwise the intrinsic reward equals 0.

12. The hierarchical reinforcement learning system according to claim 1, wherein when the disease classifier module is activated by the master module, it takes the state of the master module as input and outputs a vector which represents the probability distribution over all diseases.

13. The hierarchical reinforcement learning system according to claim 12, wherein the disease of the vector with a highest probability is returned to the user simulator module as the prediction result.

14. The hierarchical reinforcement learning system according to claim 1, wherein at the beginning of each of a plurality of dialogue sessions, the user simulator module samples a user goal from a training set randomly, and all explicit symptoms of the sampled user goal are used for initializing said each dialogue session.

15. The hierarchical reinforcement learning system according to claim 14, wherein the dialogue session will be terminated as successful if the agent simulator module make a correct diagnosis.

16. The hierarchical reinforcement learning system according to claim 14, wherein said each dialogue session will be terminated as failed if an informed disease is incorrect or a dialogue turn reaches a maximal turn, or if there are repeated actions taken by the system.

17. The hierarchical reinforcement learning system according to claim 1, wherein during a course of a dialogue session, the user simulator module interacts with the agent simulator module based on a user goal.

18. The hierarchical reinforcement learning system according to claim 1, wherein a reward shaping is used to add an auxiliary reward to the extrinsic reward.

19. A method for automatic disease prediction of a plurality of diseases with a hierarchical reinforcement learning system, the method comprising:
  modeling the acts of doctors with an agent simulator module, wherein
    the agent simulator module includes
      a master module which is in a high level, and
      a plurality of worker modules which are in a low level and
    modeling the acts of the doctors includes iteratively training each of the plurality of worker modules during a training process of the master module, wherein the iteratively training includes
      storing, for each worker module, information collected by the worker module from interacting with the user simulator module in a respective experience buffer for the worker module,
      performing experience replay to sample a subset of the collected information stored in the respective experience buffer for each worker module,
      training a current neural network for each worker module based on its respective subset of the collected information,
      updating a target neural network for each worker module based on the training, and
      removing the subsets of collected information from the experience buffers after the updating;
  modeling the acts of patients with a user simulator module, wherein the plurality of worker modules each acts as a doctor from a specific department, while the master module appoints the plurality of worker modules to interact with the user simulator module for collecting information;
  producing a prediction result of the diseases of the plurality of diseases with a disease classifier, wherein
    the master module activates the disease classifier module to output the prediction result when information collected from the plurality of worker modules is sufficient, and
    the prediction result is a probability distribution over all diseases of the plurality of diseases; and
  producing an intrinsic reward with an internal critic module,
  wherein the internal critic module is configured to generate the intrinsic reward to the plurality of worker modules judging a termination condition for the plurality of worker modules, and
  wherein the user simulator module is configured to return an extrinsic reward to the master module.

20. The method of claim 19, wherein the iteratively training includes fixing the target neural network while performing the experience replay.

* * * * *